United States Patent [19]
Long et al.

[11] Patent Number: 5,767,421
[45] Date of Patent: Jun. 16, 1998

[54] BELT CONVEYOR CROSS-STREAM SAMPLING SYSTEM

[75] Inventors: Armistead M. Long, Knoxville; John B. Long, Louisville, both of Tenn.

[73] Assignee: Heron Holdings, a Limited Liability Company, Knoxville, Tenn.

[21] Appl. No.: 475,068

[22] Filed: Jun. 7, 1995

[51] Int. Cl.$^6$ .................................................. G01N 1/12
[52] U.S. Cl. ........................... 73/863.55; 73/863.92
[58] Field of Search ............................ 73/863.91, 863.92, 73/863.56, 863.53, 863.55, 864.32

[56] References Cited

U.S. PATENT DOCUMENTS

| | | | |
|---|---|---|---|
| 3,393,567 | 7/1968 | Jirik | 73/863.55 |
| 4,619,149 | 10/1986 | Long | 73/863.91 |
| 4,796,476 | 1/1989 | Long | 73/863.91 |
| 4,884,462 | 12/1989 | Long | 73/863.91 |
| 4,919,000 | 4/1990 | Long | 73/863.91 |
| 4,955,242 | 9/1990 | Long | 73/863.91 |
| 5,392,659 | 2/1995 | Ford, Jr. et al. | 73/863.56 X |

FOREIGN PATENT DOCUMENTS 832396  5/1981  U.S.S.R. ............... 73/863.91

OTHER PUBLICATIONS

Garland Impact Idlers, Jul. 1994, John B. Long Co., PO Box 50608, Knoxville, TN 37950–0608. 2 pages.
Belt Conveyor Idler Index, 1990, FMC Corporation. pp. 63, 65, 67 & 4 other pages.
H–Plus Series Heavy Duty Belt Conveyor Idlers, Continental Conveyor & Equipment Company, PO Box 400, Winfield, AL 35594. 3 pages published by Sep. 1995.
Hewitt–Robins Idlers, 1987, Hewitt–Robins, Corp. 3 pages.
Precismeca Idler Manual, Catalogue #193, Kevin K. Hays, North American, Inc. Transall Division, Elm Street, Helena Industrial Park, PO Box 633, Helena, AL 35080. Published by Sep. 1995 pp. 40–42 plus 2 other pages.
Prok Hi–Balance Conveyor Idlers, 1985, Prok Group Limited, Design and Manufacturing Engineers, PO Box 465, Mulgrave North, 3170. pp. 1–5, 59–61.
Belt Conveyor Idlers and Components, Catalog 101, Goodman Conveyor Co., PO Box 866, Route 178 South/Belton, South Carolina 29627, published by Sep. 1995 pp. 52–55 plus two other pages.
Lord Industrial Products, 1993, Industrial Products Division, 1952 West Grandview Blvd., PO Box 10040, Erie, PA 16514–0040. pp. 64–65 plus 1 additional page.
Clean Sweep AutoSampler Series, John B. Long Co., PO Box 50608, Knoxville, TN 37950–0608. 2 pages Published by Sep. 1995.
Clean Sweep Sampling System, John B. Long Co., PO Box 50608, Knoxville, TN 37950–0608. Nov. 1993 2 pages.
Clean Sweep Sampling System, Planning a Clean Sweep Sampler Installation, John B. Long Co., PO Box 50608, Knoxville, TN 37950–0608. 6 pages Published by Sep. 1995.
QHS Mechanical Sampling Systems & Laboratory Preparation Equipment, Quality Handling Systems Pty. Ltd., 184 Newton Road, Wetherill Park, N.S.W. 2164 Australia. 3 pages Published by Sep. 1995.
Sampling and Sample Preparation, Glen Creston, 16 Dalston Gardens, Stanmore, Middx.d HA7 1DA. p. 4 pages Published by Sep. 1995.

*Primary Examiner*—Thomas P. Noland
*Attorney, Agent, or Firm*—Luedeka, Neely & Graham, PC

[57] ABSTRACT

A method and apparatus is provided for cross-stream sampling of bulk material distributed as a mounded continuum in a trough formed along the length of a belt conveyor. A rotating cutter passes transversely through the traveling, bulk material continuum to extract substantially all material on said belt in a swath between transverse, parallel cutting planes. Proximate of the sample cutting swath, before and after such swath relative to the material traveling direction, rigid skirting is provided to overlay both lateral edges of the belt. Garlands of resiliently mounted belt supporting idlers span under the belt laterally of the swath to urge the belt into a substantially continuous line of sealed contact with the skirting. Simultaneously, the trough bight of the belt between the skirting is urged into the swath volume to require displacement from the swath volume by passage of the sample cutter thereby insuring full belt surface contact by the cutter and maximum small particle retrieval.

15 Claims, 9 Drawing Sheets

BELT CONVEYOR CROSS-STREAM SAMPLING SYSTEM

BACKGROUND OF THE INVENTION

This invention relates to improvements in bulk material sampling machines and methods. In particular, the invention relates to a more effective system and apparatus for extracting a substantially complete cross-stream sample of bulk material distributed as a continuum along a traveling, belt formed trough.

The invention was primarily developed for use in the collection of analysis samples from a coal conveyor line therefore making the objectives, procedures, systems, methods and apparatus more conveniently and expansively described relative to that application. It will be appreciated, however, that the invention is applicable to all belt carried bulk materials such as ores and grains and is not to be in any way construed as limited to the sampling of coal and coke.

A prudent coal user wants and expects that coal shipped to him by a supplier have certain characteristics as to size, volatility, moisture content, BTU value, etc. in accordance with his needs. Thus, a supply contract may provide for representative sampling of the coal shipment by the supplier, at the source, and again, by the user, on delivery. Furthermore, coal is a difficult material to sample. A production conveyance stream frequently will include both large and small lumps, of various sizes and shapes, down to dust size particles. Moreover, such lumps and particles may vary in composition from noncombustible to completely combustible.

The most difficult sampling problem to overcome is the tendency of such bulk materials to segregate by particle size during handling. Accordingly, fine particles tend to concentrate in the middle and toward the center of piles or distribution continuums on belt conveyors. Larger particles tend to run to the outer edges of such piles.

When mechanical cross-section sample cutters fail to remove all material in the sample swath, the remaining material is likely to be concentrated among the smaller particles. Consistent recovery of a higher percentage of larger particles than smaller particles represents a distribution bias. Such samples, therefore would not represent an actual material production stream distribution by particle size.

It is, therefore, one principle objective of the present invention to optimize physical contact between the bottom of a sample cutter and the top surface of a corresponding conveyor belt and thereby maximize removal of all material on the belt within the sample cutter swath.

Another principle objective of the invention is the optimization of physical contact between the bottom of the belt side skirting and the carrier face of the belt and thereby minimize the loss of material between the belt and the skirts.

A further objective of the present invention is to achieve maximum removal by a mechanical sampler of all particles present in cross-sections of a bulk material continuum distributed along a moving belt. This objective is particularly relevant to fine particles which might otherwise adhere to the belt surface.

Still another objective of the present invention is to confine the cross-sectional position of a longitudinally traveling bulk material transport belt through the scoop swept volume of a rotatively driven scoop whereby the belt must be displaced from the sweep volume by the rotating scoop to complete the sample extraction.

An additional objective of the present invention is to train the course of a compliant, bulk material transport belt into a substantially circular arc as the belt crosses a sampling swath section, the normal radius of the arc being slightly less than the arc radius corresponding to a cooperating material sample scoop whereby the small interference portion of the belt is pliantly displaced from the scoop sweep space as a cross-sectional sample of the bulk material carried by the belt is extracted.

A still further objective of the present invention is to reduce the potential for sample bias in cross-section samples extracted from a bulk material transport belt.

SUMMARY OF THE INVENTION

These and other objects of the invention, as will become apparent from the following description, include a method of removing cross-sectional samples of bulk material from a carrier belt comprising the steps of resiliently biasing the carrier belt into a spacial volume between cross-sectional planes that is abruptly swept of bulk material by rotating structure so that the belt carrier surface must be displaced from the spacial volume by said structure rotation.

The apparatus of the invention includes means for removing a cross-sectional sample of bulk material carried in a traveling trough formed by a moving conveyor belt that is at least partially supported by inner and outer idlers. The invention includes a sample cutter that is rotatively driven about an axis aligned parallel with the trough traveling direction and located above the trough. Radial extremities of the cutter structure traverse a circular arc about the rotational axis through the belt trough to extract substantially all the bulk material on the belt in a swath space between a pair of cutting planes that are substantially transverse to the belt traveling direction. Longitudinal belt skirting is disposed adjacent the cutting planes to overlie the belt edges which are guided by garlands of belt supporting idlers located beneath the belt and adjacent the cutting planes spaced longitudinally from the swath space. The garlands are suspended from resilient support points located on opposite sides of the belt. Cooperatively, the garlands and their resilient supports bias the normally loaded position of the belt trough up into the cutter swath space to be displaced by the arcuate swing of the cutter. Such resilient bias by the garland idlers also presses the belt against the longitudinal belt skirting as firmly as possible considering load induced sag of the belt between garlands for the purpose of preventing material spillage during sampling. A scraping/scooping relationship between the cutter and the belt surface results which is calculated to remove all particles on the belt surface.

As an additional and unobvious consequence of the resilient garland idler support of the belt, increased material weight on the belt deepens the belt transverse trough thereby pulling the belt edges more tightly against the longitudinal skirting.

This designed contact between the sample cutter and the conveyor belt is a new concept that is in contrast with a prior operational objective which avoided such contact. Previous cross-sectional sampling machine designs were aimed at producing top-of-the-belt cutter sweep profiles that were concentric with, but not touching, the belt. Such older designs utilized flexible attachments to the back of the cutter having an intended function of wiping the belt clean. However, these flexible attachments have been found to be of limited effectiveness.

Taking advantage of the fact that the rubber surfaces of bulk material conveyor belts are designed for long life under hostile conditions, the light rubbing contact of the belt by the cutter and skirting edges as proposed herein does not greatly increase or aggravate operational wear problems and may actually reduce such wear stemming from particles being confined and ground between two moving surfaces.

BRIEF DESCRIPTION OF THE DRAWINGS

Preferred embodiments of the invention will hereafter be described relative to the accompanying drawings wherein like reference characters designate like or similar elements throughout the several figures of the drawings in which.

DESCRIPTION OF THE PREFERRED EMBODIMENTS

Figure 1:
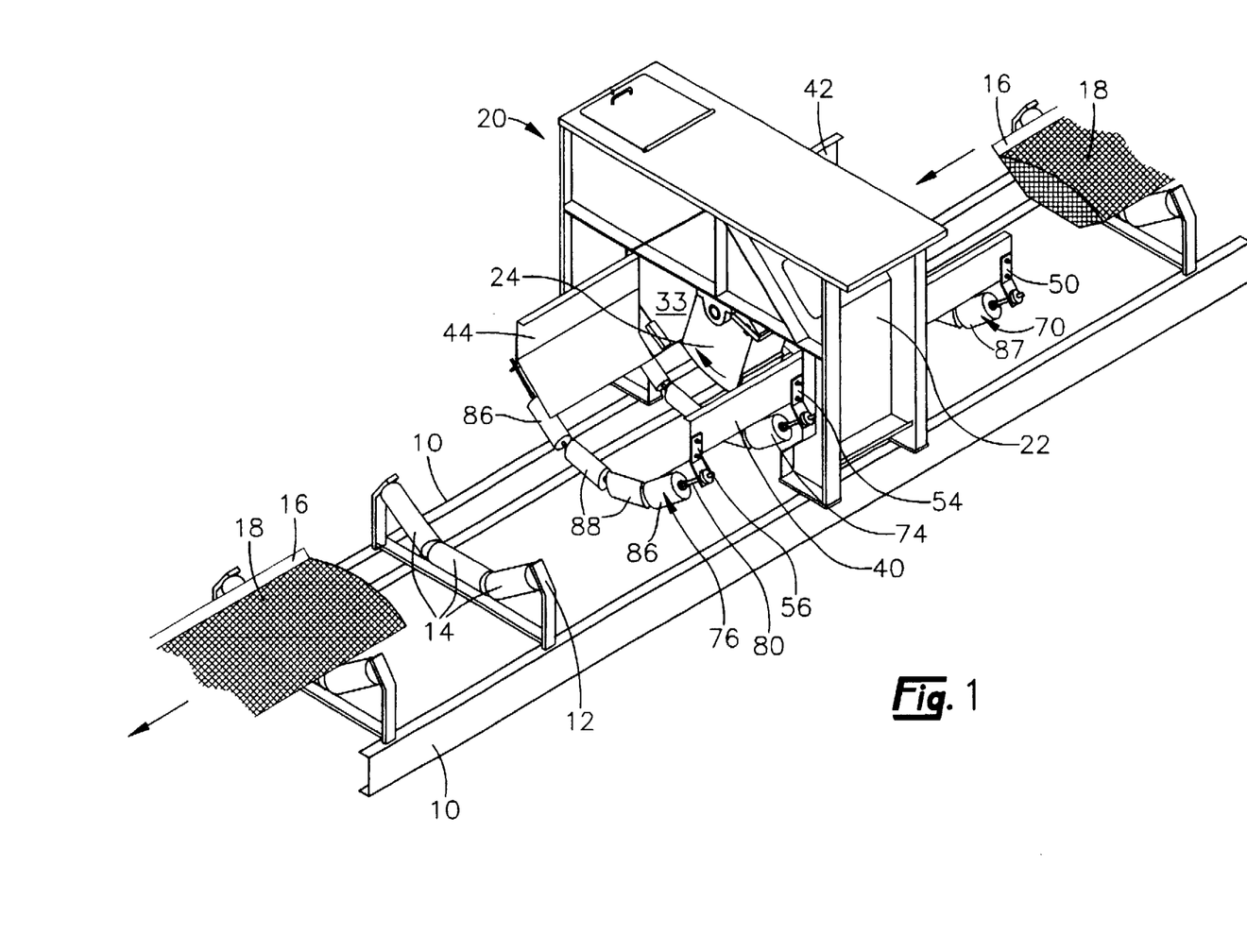
FIG. 1 is an isometric view of a cross-sectional sampling station having surge bin skirting and garland impact idlers in assembled association with a bulk material belt conveyor.
Figure 2:
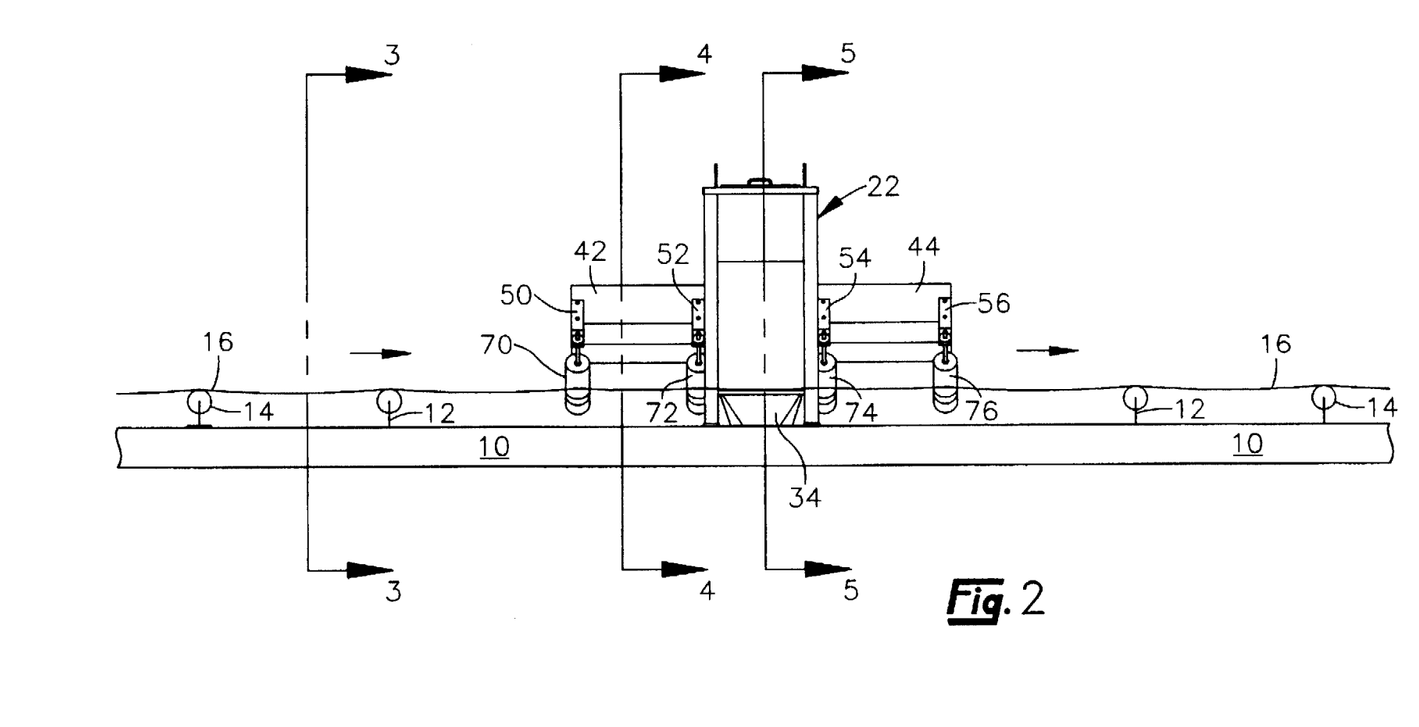
FIG. 2 is a side elevational view of the cross-sectional sampling station of FIG. 1.
Figure 3:
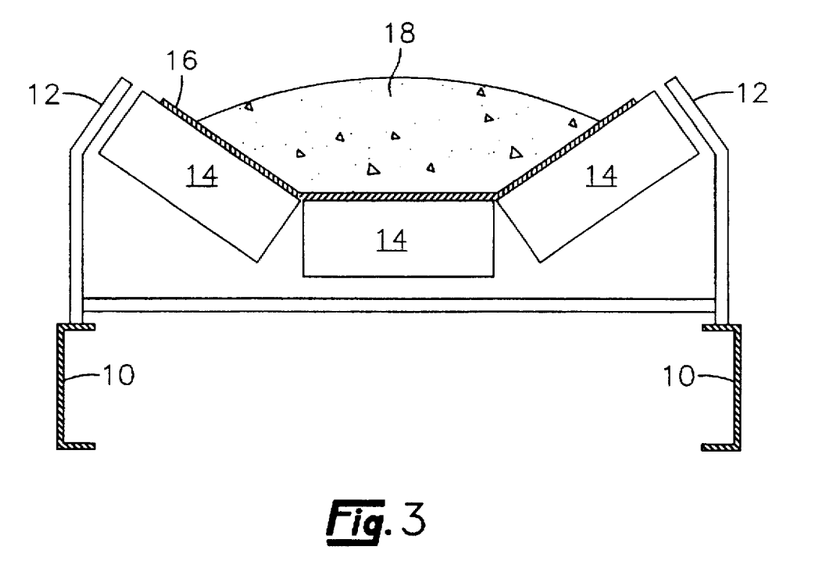
FIG. 3 is a sectional view of the sampling station represented by FIG. 2 as viewed along cutting planes 3—3.

Referring to FIG. 1, a typical belt conveyor assembly for transporting bulk material is shown to include a pair of laterally spaced, parallel stringers 10. Such stringers are primary structural support elements shown here as channel sections but may also be angle or I sections.

Belt supporting idlers 12 transversely bridge the stringer separation space, usually at 3 ft. to 5 ft. longitudinal spacings depending on the projected belt load and belt tension. By traditional design conventions, full load allowable sag in the belt may vary from about three-quarters of an inch for a three foot longitudinal spacing to about one and one-quarter inch for five foot longitudinal spacing between the idlers 12.

As shown by FIG. 1, the idler units 12 may comprise three, freely rotating idler elements 14 of substantially equal length. The middle idler in such a set rotates about a substantially horizontal axis whereas the two outer idlers rotate about axes aligned at about 20° to 45° to the center idler axis. A 35° angle of the outer idler axis is the more common configuration. The idler axes may be rigidly positioned from pedestals or stanchions as illustrated or garland suspended between brackets as to be further described. When overlaid by a flexible, rubber surface coated conveyor belt 16, the included angle between the two outer idler elements 14 cross-sectionally form the belt 16 into an elongated trough for carrying a mounded continuum of bulk material 18 such as coal or ore.

In the preferred embodiment of the invention, the cross-sectional sampling assembly is an integral unit 20 secured to the conveyor stringers 10 at a convenient location in place of one or more idlers 12. Such an assembly comprises a housing 22 superstructure which supports and unitizes the other elements of the assembly. Foremost among such other elements is the sample cutter subassembly 24.

The cutter subassembly 24 comprises a three wall box 26 having an open bottom and front end face. The bottom edges 28 of the box 26 side walls are radial about the cutter rotational axis 30. This rotational axis 30 is substantially parallel with the belt 16 traveling direction and located slightly off-center above the belt toward the sample discharge chute 34. Bearing pedestals 32 anchored to the housing 22 positionally secure the cutter rotational axis. In operation, the cutter box 26 is usually driven about a full 360° rotational circle by power and drive means not shown to extract a cross-sectional swath of belt carried material 18 and deposit the extracted material into the sample discharge chute 34.

In operative support of the cutter subassembly is the belt skirting comprising three independent rigid panels 40, 42 and 44. Along the near edge of the belt 16, the skirt panel 40 is continuous for about eight feet, for example, distributed symmetrically upstream and downstream of the housing 22. On the sample exit side of the belt 16, respective panel sections 42 and 44 are provided upstream and downstream of the sample exit 33 with an unobstructed opening in the cutter swath from the belt surface into the sample delivery chute 34.

Figure 4:
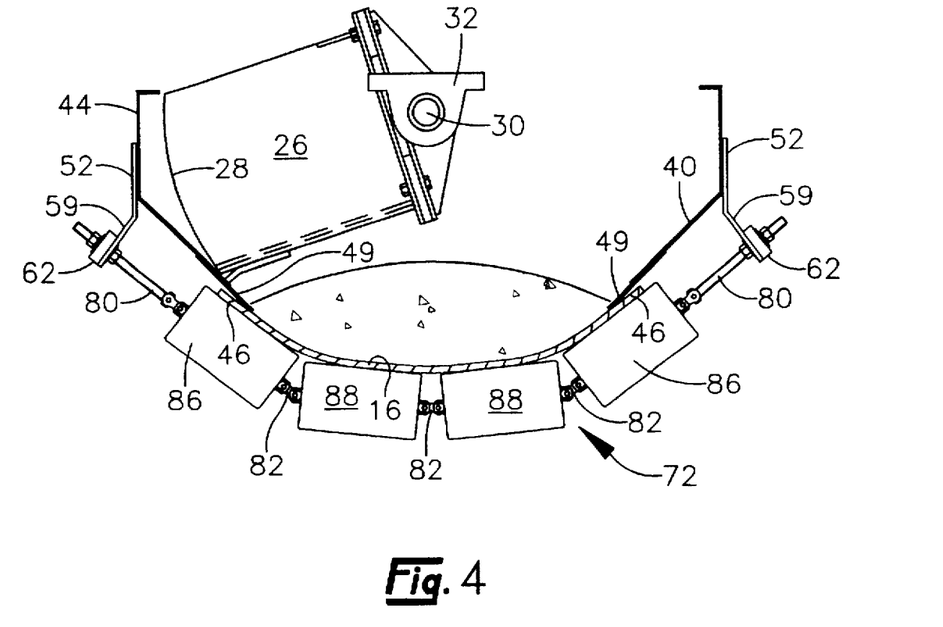
FIG. 4 is a sectional view of the sampling station represented by FIG. 2 as viewed along cutting planes 4—4.
Figure 5:
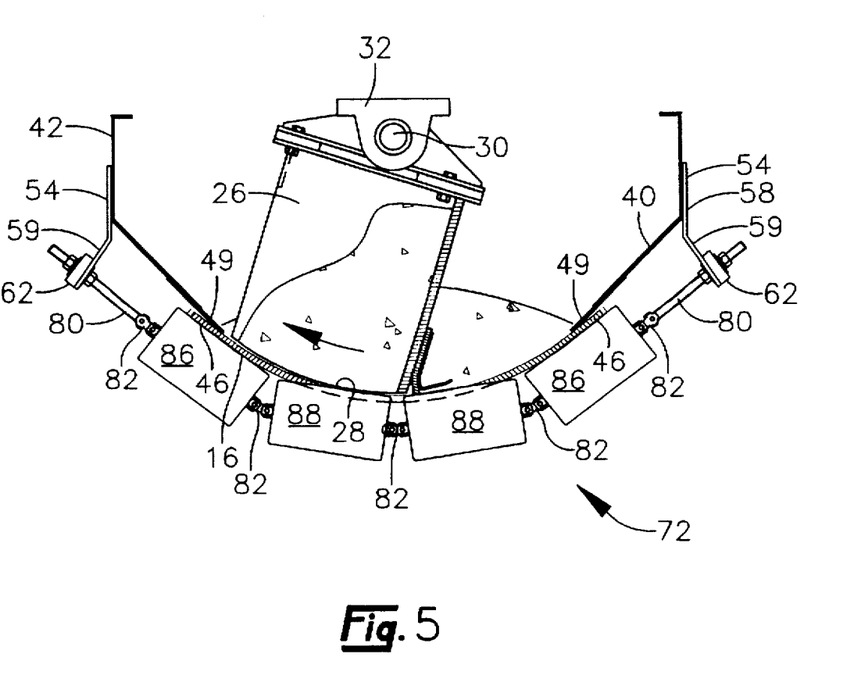
FIG. 5 is a sectional view of the sampling station represented by FIG. 2 as viewed along cutting planes 5—5.
Figure 6:
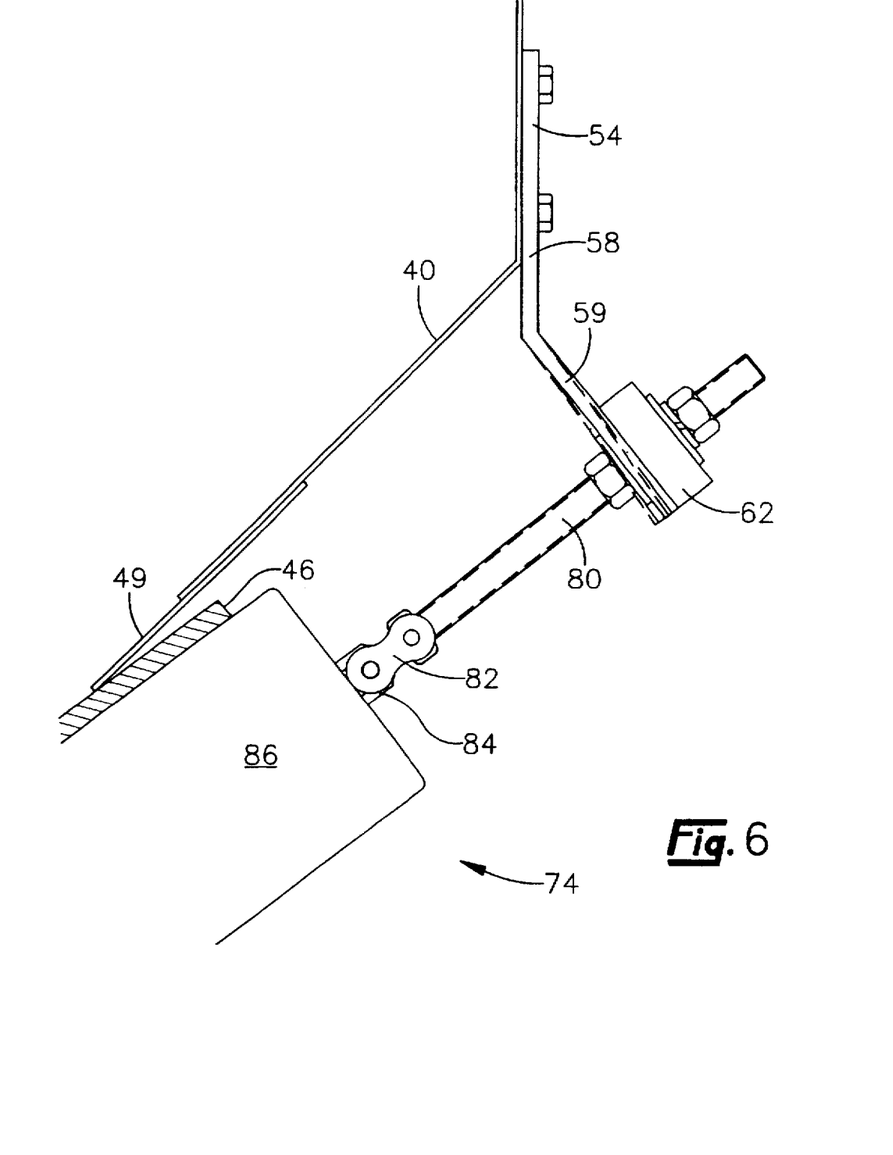
FIG. 6 is a detailed enlargement of the garland idler mounting arrangement.

As will be noted from FIGS. 4, 5 and 6, each skirt panel comprises a vertical splash plate section and a lower lip section 49 which overlaps the upper edges 46 of the belt 16. All three skirting panels are attached to the housing 22 with adjustable outboard supports not shown to set the lower lips 49 in mutual parallelism at the desired height above the rails 10.

At as many points along the skirting panel as desired are pairs of garland idler support brackets 50, 52, 54 and 56. Each of these support brackets includes a base leg 58 anchored to the skirting panel splash plate and a spring leg 59 cantilevered therefrom. Near the end of the spring leg 59 is an aperture 60 which receives an elastomer bushing 62. A rod sleeve 64 located coaxially along the bushing axis is bonded to the elastomer. This elastomer bushing 62 and sleeve 64 cooperate with end terminals 80 (FIGS. 6 and 7) respective to each of four, belt supporting garland idlers 70, 72, 74 and 76. The end terminal 80 of each idler set is a threaded rod that is pivotally connected by links 82 to the proximate axle end 84 about which the respective outer edge idler 86 of the garland set rotates. With reference to FIG. 4, it is seen that by the same means of pivot links 82, the inside garland idlers 88 are rotatably chained to the outer edge idlers 86 and to each other.

Although 3-element idler units are normally used to support the belt 16 along the main transport line, 4 to 6 element garland assembled units are preferred for the sampling assembly 20. Shorter idlers with smaller shaft lengths reduce the bearing loads on each idler and hinge links between adjacent idler elements absorb impact stress.

Figure 7:
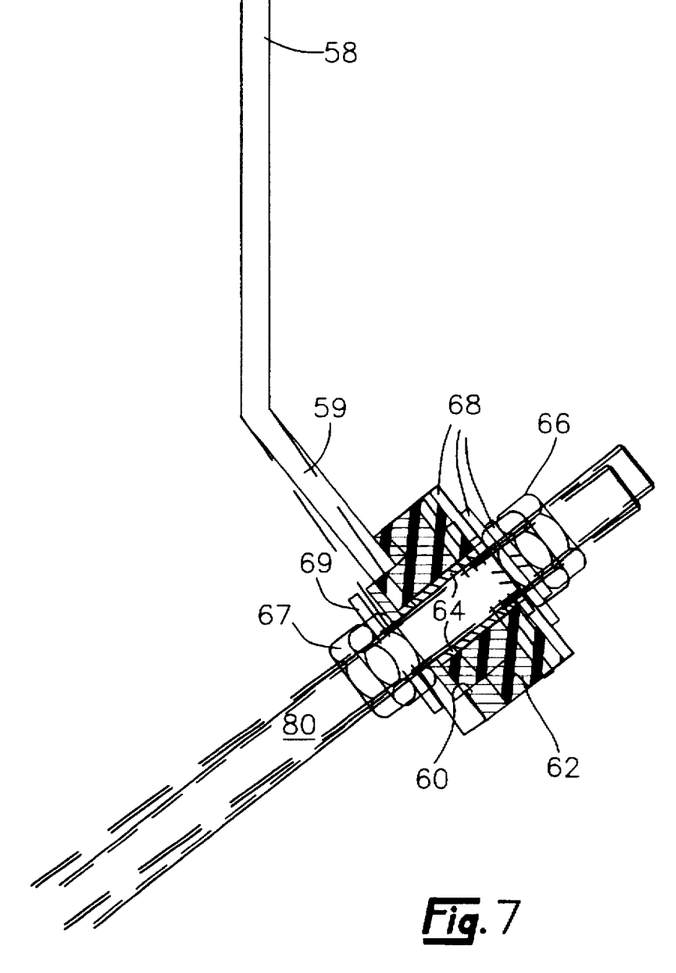
FIG. 7 is an enlargement of the garland attachment showing movement of the bonded rubber mounts.

Relative to FIG. 7, threaded nuts 66 and 67 clamp washers 68 and 69 against the sleeve 64 on opposite faces of the spring leg 59 to confine the elastomer bushing 62 leaving the bushing free to resiliently distort from axially applied stress only in the radial direction. Collective positionment of the nuts 66 and 67 along the length of rod 80, however, serves to adjust the effective length of the garland catenary between opposite support brackets. As the garland catenary length is reduced, increased tension along the garland idler linkage draws the belt 16 more tightly against the skirting and increases the belt trough bight radius.

It is to be emphasized that the inside garlands 72 and 74 are located along the belt 16 traveling direction alongside the transverse cutting planes defined by the rotational swath of cutter 24 but outside of the swath space. Garland 72 is upstream of the cutter swath and garland 74 is downstream of the swath. No structure other than the belt 16 is in the swath space and substantially no structural support means bearing weight of the carrier belt is located between the parallel planes that delineate the rotational swath space of the cutter 24.

When tensilely stressed, each garland end terminal supporting spring leg 59 will yield in the manner represented by the dashed line configuration of FIG. 7. Additionally, each garland end terminal will further yield under stress by the axial compliance of the bushing 62 that corresponds with the previously described radial distortion. Collectively, therefore, the cantilever spring leg 59 and elastomer bushing 62 represent two, serially connected spring supports for the garland end terminal, each of a respective spring rate. The support surface line of a garland idler assembly is adjusted so that the arc of the cutter radius about axis 30 overlaps the arc of the material support surface of the belt 16. This relationship is graphically represented by FIG. 8 which, by line A, illustrates in full line sectional profile the circular arc coursed by the swing of the cutter 24 whereas dashed line B represents the belt 16 carrier surface position when loaded and dashed line C represents the belt carrier surface position when empty.

Figure 8:
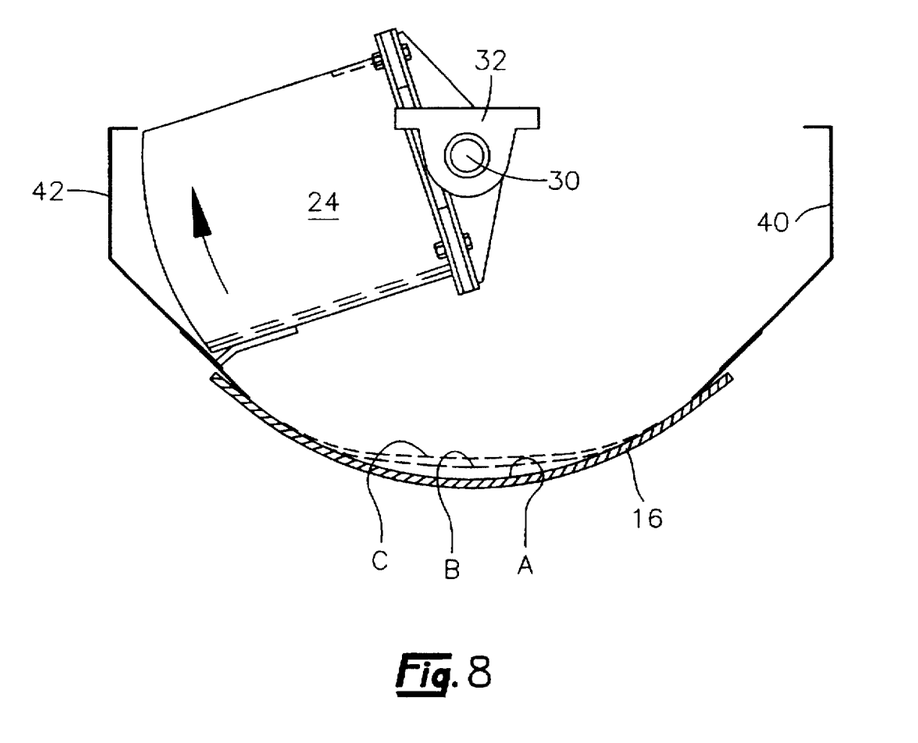
FIG. 8 is a sectional view of the sampling station represented by FIG. 2 as viewed along cutting planes 5—5 showing contrast between an empty belt, a loaded belt and the belt during a sweep of a sample cutter.

When rotated, the cutter 24 contacts the belt 16 carrier surface and pushes it down in a shallow crescent of interference. Displacement of the belt surface produces a trampoline effect between the cutter 24 and the belt 16 to suspend the sample material followed by a scraping, scooping effect by the cutter. The collective effect is to suspend, mobilize and extract substantially all the particles on the belt within the volumetric swath of the cutter.

Vertical displacement of the belt 16 also results in inward flexure of the garland idler suspension springs 59. Without significant vertical flexure of the support brackets, light contact between the surface of the belt and the bottom edge of the skirting is maintained despite belt displacement at the center of the arc.

In an example of the invention using a 42 inch wide belt, approximately 0.25 inch downward movement by each of the suspension points will permit approximately 0.50 inch of downward movement in the altered arc at the center of the adjacent garland idler units 72 and 74. From this example, it could be recommended that the garland idler arc be adjusted so that the surface of a 42 inch belt 16 interferes with the cutter radius by about 0.5 in.

Approximately 86% of the belt 16 load weight is concentrated over the center idler elements. Consequently, most flexing between elements occurs between center elements. Also, there is a tendency of the joints between inner and outer idler elements to straighten.

A further design characteristic of a preferred embodiment of the invention is alignment of the cutter 24 rotational axis 30 slightly off-center with regard to the longitudinal center plane of the belt 16 so that skirting 40 on the belt side opposite from the discharge chute 34 is not contacted. There is no skirting in the cutter swath on the discharge chute side of the belt. The belt 16 carrier surface across the cutter swath width is neither concentric with the cutter arc about axis 30 nor symmetrical with the cutter arc of rotation.

The catenary curve of a garland idler has the greatest radius from a point midway of the belt travel. Cutter movement 24 forces the belt down into a crescent shape area variation from the original support profile. Upward spring rebound within this crescent shaped area of transverse belt flexure assures the desired scraping, scooping contact relationship between the moving cutter 24 and moving belt 16.

Tests with the invention tend to confirm speculations that a cutter 24 sampling cycle which contacts the belt 16 as it crosses the material continuum 18 may require less energy than a prior art configured effort of only skimming the belt carrier surface due to the consequences of climbing and pushing over particles at a level above the belt surface. The power required for the cutter to displace the belt from under the surface particles appears to be insignificant.

Theoretically, minimum thrust force is required if the cutter 24 gets under the material bed and does not have to push through the interlocking, irregularly shaped particles. The force required to push the belt away from the material bottom layer appears more than offset by the reduction of cutter thrust requirements for maintaining contact, albeit light contact, between the belt carrier surface and the bottom of the cutter.

Also, less thrust seems to be required if the belt can be displaced as required for the cutter to pass over particles which might otherwise wedge between the cutter and the belt. Continuous, flexible upward support for the belt provided by the spring mounted garland idlers quickly restores contact after an interference particle has been passed over.

In addition to the operational efficiencies noted above, the present invention also simplifies the field installation and final operating adjustments of a cross-stream sampling facility. The assembly housing 22, belt skirting 40, 42 and 44, and garland idlers 70, 72, 74 and 76 are all part of the overall unit.

Sampling station fabrication includes a shop assembly procedure wherein the skirting 40, 42 and 46 is secured to the sampler housing 22 and adjusted so that the cutter 24 just misses the edge of the near side panel 40. The sample exit side skirting 42 and 43 would then be adjusted to the same height relative to the sampler housing 22. Next, the garland idlers 70, 72, 74 and 76 would be assembled with respective brackets 50–56 and bolted to the previously assembled skirting. The idler support brackets 50–56 are vertically positioned on the skirting to touch the garland idler elements 86 lightly against the skirting edges on both sides. Adjustment between the brackets 50–56 and the garland end terminal rods 80 may be locked in place with double nuts. The aforedescribed shop assembled unit is shipped to the operating location without subsequent disassembly.

At the operational location, the garland idler assemblies with brackets 50–56 are removed from the skirting without further disassembly. This permits the sampler housing 22 unit to be secured to the conveyor stringers 10 without parting the belt 16. Four outboard supports (not illustrated) for the skirting 40–44 are secured between the skirting and stringers. Finally, the garland idlers and brackets are reinstalled by bolting the brackets back to the skirting with vertical adjustment such that the belt surface is in contact with the bottom edges of the skirting.

Figure 9:
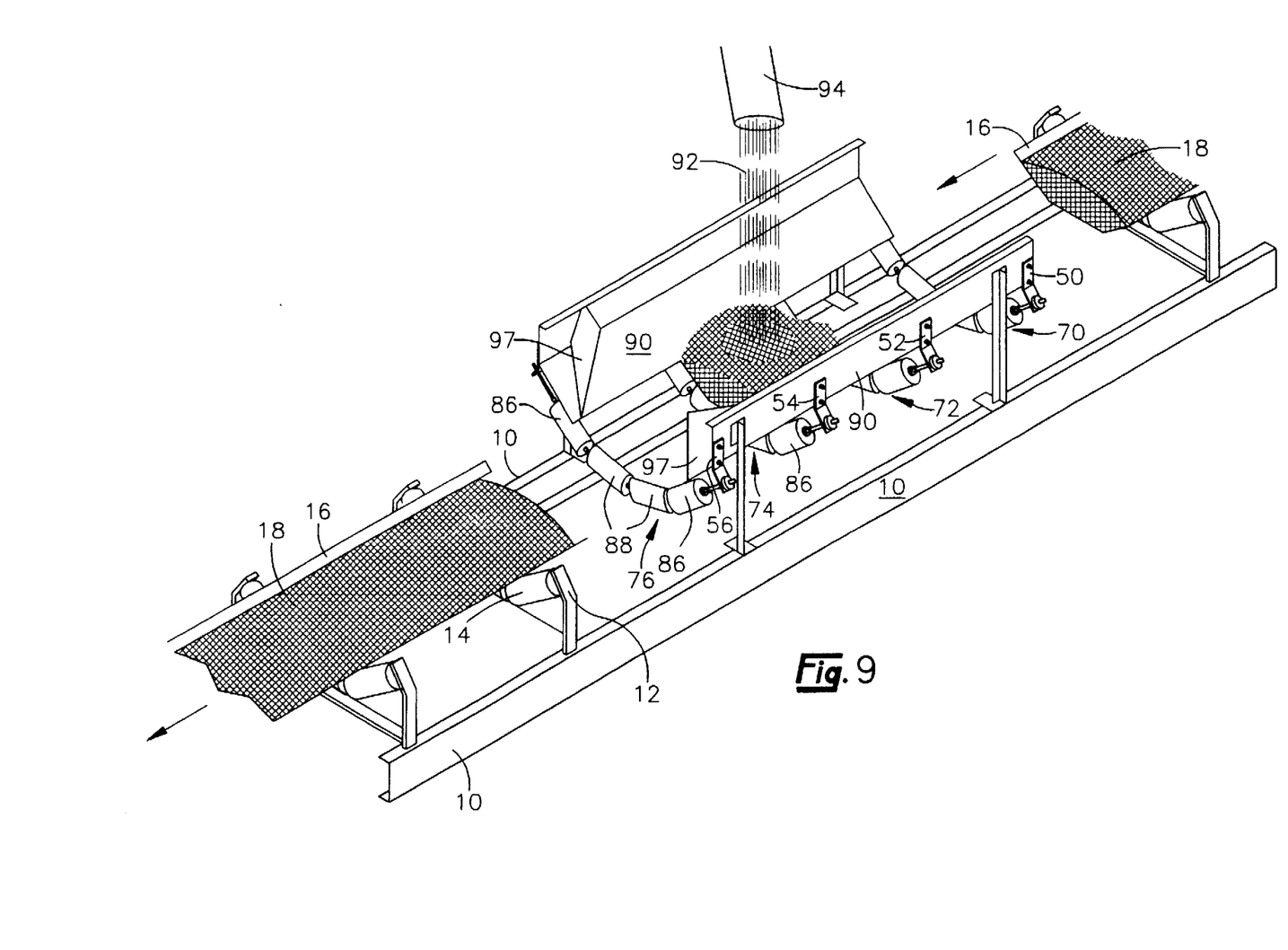
FIG. 9 is an isometric view of a material transfer station having the surge bin skirting and cooperating garland impact idlers in assembled association with a bulk material belt conveyor.

Independent of the sample cutter, the skirt supported garland edler combination provides a superior material transfer station as shown by FIG. 9 wherein cooperation between the skirting 90 and garland idlers 70, 72, 74, and 76 prevents spillage of added material 92 while being transferred from a tributary delivery source 94 onto the primary carrier belt 16. The two continuous pieces of skirting 90 along opposite sides of the belt 16 are supported by and attached to the conveyor stringers 10. From the skirting are suspended two or more garland idler assemblies 70, 72, 74 and 76 using flexible brackets 50, 52, 54, and 56, respectively. The belt 16 is routed between the lower edge of the skirting 90 and the rotating surfaces of the outer edge garland elements 86. The skirting sides 90 prevent surges of the added material 92 from spilling over the sides of the belt 16. Excess added material is contained between the opposite side skirts 90 until the moving belt can accommodate the excess. Flow guides 97 secured to the skirting 90 at the downstream end thereof assist in shaping the deposited material 92 into a smoothly mounded continuum carried along the belt 16. Additional weight of the added material causes the outer garland idler elements 86 to press the belt 16 more tightly against the lower edges of the skirting 90 to intensify the belt seal and further prevent spillage of the added material. As described with respect to FIG. 8, the flexible mounts 96 that secure the garland idler assemblies to the skirting 90 allow the skirting to maintain contact with the belt 16 as loads on the belt are changed.

When installed, the garland idler assemblies are adjusted for light contact between the surface of an empty belt and the bottom edge of the skirting 90. As load is applied, more than 80 percent of the load is likely to be on the center elements 88 thereby increasing the sag deflection of the belt along the center. This increased sag deflection decreases the relative joint angles between the center elements 88 and the outer elements 86. Such decreased angle tends to lift the outer elements 88 and thereby increase contact pressure between the top surfaces of the belt 16 and the bottom edge of the skirting 90.

Although particular embodiments of the present invention have been described in the foregoing detailed description, it will be understood that the invention is capable of numerous rearrangements, modifications and substitutions without departing from the scope and spirit of the invention as set forth in the claims below:

As our invention,
We claim:

1. An apparatus for removing a cross-sectional sample of bulk material carried in a traveling trough formed by a moving conveyor belt at least partially supported by bottom and edge support idlers, said apparatus comprising cutter means driven rotatively about an axis above said trough and substantially parallel with a traveling direction of said moving belt, radial extremities of said cutter means traversing a circular arc through said trough to extract substantially all bulk material on said belt in a swath space between a pair of cutting planes that are substantially transverse of the belt traveling direction, opposite longitudinal edges of said moving belt being guided beneath longitudinal skirting adjacent said cutting planes, garlands of belt supporting idlers disposed beneath said belt adjacent said cutting planes and spaced longitudinally from said swath space, said garlands being resiliently suspended from support points on opposite sides of said belt to bias the normal loaded position of said belt trough into said cutter means swath space whereby said belt is displaced from said swath space by arcuate traversal of said cutter means.

2. An apparatus as described by claim 1 wherein said garland lengths between the opposite side resilient supports are adjustable.

3. An apparatus as described by claim 1 wherein said belt is free of all structural support between said cutting planes.

4. An apparatus as described by claim 1 wherein said belt edges are resiliently biased by said garlands into sealing contact with an underside of said skirting.

5. Apparatus as described by claim 1 wherein each belt supporting garland adjacent said cutting planes comprises a plurality of idler elements, each being rotatable about a rigid axle segment, each axle segment being pivotally linked at respective ends to adjacent axle segments.

6. A method of removing a cross-sectional sample from a traveling continuum of bulk material distributed along a trough formed by a pliable carrier belt, said method comprising the steps of abruptly sweeping the spacial volume of said bulk material continuum between spaced cross-sectional planes by rotating structure to remove substantially all material on said belt within said volume and resiliently biasing a portion of the material supporting surface of said carrier belt into said spacial volume whereby the resiliently biased portion of the material supporting surface must be displaced from said spacial volume by said structure rotation.

7. A method as described by claim 6 wherein skirting is provided to overlay opposite lateral edges of said belt in the proximity of said volume, said belting being resiliently biased against said skirting.

8. A method as described by claim 7 wherein the resilient bias of said belting against said skirting is provided by spring mounted garlands of idlers supporting said belt.

9. An assembly for extracting a cross-section sample of bulk material from a continuum of such material distributed along the trough of a conveyor belt moving in a transport direction, said assembly comprising a housing disposed above and across said conveyor belt for supporting a rotary sample cutter, said sample cutter being rotatively driven about an axis aligned substantially parallel with said transport direction, opposite lateral sides of said housing having belt skirting means secured thereto for overlying lateral edges of said belt, resilient hangers secured to said skirting means for suspending ends of garland connected idlers, said garland connected idlers being disposed under said belt for supporting said belt in running contact with said skirting means and in the sample extracting rotational path of said cutter.

10. An assembly as described by claim 9 wherein the length of said garland connected idlers is adjustable between hangers respective to opposite sides of said belt.

11. An assembly as described by claim 9 wherein said housing comprises a sample exit opening adjacent said belt and in the rotational path of said cutter for receiving the bulk material sample extracted from said continuum.

12. An assembly as described by claim 11 wherein said skirting along said belt is discontinuous across the rotational path of said cutter adjacent said sample exit opening.

13. An apparatus for removing a cross-sectional sample from a traveling continuum of bulk material distributed along a trough formed by a pliable carrier belt upper support surface, said apparatus comprising: sample collection means having rotational movement between spaced, parallel planes traversing a segment of said carrier belt, such movement of said sample collection means sweeping said collection means along a spacial volume transverse of said belt and between said parallel planes; and, resilient bias means to resiliently guide said belt upper support surface into and across said spacial volume whereby said belt upper support surface must be displaced from said spacial volume by rotational passage of said sample collection means to remove substantially all bulk material on said belt within said spacial volume.

14. An apparatus as described by claim 13 wherein said resilient bias means also supports a portion of the carrier belt weight and forms said trough in the upper support surface of said belt.

15. An apparatus as described by claim 13 having substantially no structural support means bearing weight of said carrier belt between said parallel planes.

* * * * *